| United States Patent [19] | [11] Patent Number: 4,639,421 |
|---|---|
| Sage, Jr. | [45] Date of Patent: Jan. 27, 1987 |

[54] FLUORESCENT GRAM STAIN

[75] Inventor: Burton H. Sage, Jr., Raleigh, N.C.

[73] Assignee: Becton, Dickinson and Company, Franklin Lakes, N.J.

[21] Appl. No.: 656,617

[22] Filed: Oct. 1, 1984

[51] Int. Cl.$^4$ .................... C12Q 1/04; C12Q 1/14; C12Q 1/10

[52] U.S. Cl. ................................ 435/34; 435/36; 435/38

[58] Field of Search .................. 435/29, 34, 36, 37, 435/38, 822, 849, 875, 852, 851, 871; 424/3

[56] References Cited

U.S. PATENT DOCUMENTS

| 4,094,745 | 6/1978 | Scholefield | 435/36 |
|---|---|---|---|
| 4,126,516 | 10/1978 | Messing et al. | 195/103.5 R |
| 4,225,669 | 9/1980 | Melnick et al. | 435/34 |
| 4,508,821 | 4/1985 | Mansour et al. | 435/39 |

OTHER PUBLICATIONS

Matsuyama, Federation of European Microbiological Societies Microbiology Letters, vol. 21, 1984, pp. 153–157.

Boge et al. Journal & General Microbiology (1983), vol. 129, pp. 973–980.

Stohr et al., Histochemistry, vol. 51, 1977, pp. 305–313.

Govoronov et al., Mikrobiologiya 1982, vol. 51, No. 5 pp. 731–734.

*Primary Examiner*—Esther M. Kepplinger
*Assistant Examiner*—William J. Herald
*Attorney, Agent, or Firm*—Richard E. Brown

[57] ABSTRACT

A method to determine the Gram sign of microorganisms includes staining the microorganisms with a plurality of fluorescent dyes in the presence of a staining buffer, applying excitation energy to the stained microorganisms, observing the color of the fluorescence emission of the stained microorganisms, and assigning the positive Gram sign to microorganisms which fluoresce substantially green and the negative Gram sign to microorganisms which fluoresce substantially orange.

10 Claims, No Drawings

FLUORESCENT GRAM STAIN

BACKGROUND OF THE INVENTION

1. Field of the Invention

This invention relates to the staining of mircroorganisms. More particularly, it relates to the detemination of the Gram sign by staining the microoganisms with a fluorescent dye combination.

2. Description of the Prior Art

The Gram stain is one of the most widely used and important stains in microbiology. It permits the differentiation of microorganisms into two groups, conventionally referred to as Gram-positive and Gram-negative, based on the color of the stained organism at the conclusion of the staining protocol. In the Gram stain procedure, microogranisms on a cover slide are contacted with aqueous crystal violet, treated with iodine-potassium iodide solution, decolorized with alcohol or an ether-acetone mixture, counterstained with safranin O, dried, and examined. Gram-positive microogranisms retain the crystal violet and are thereby stained blue-violet. The Gram-negative microogranisms are completely decolorized by the organic solvent and show only the red color of the subsequently applied counter-stain.

The determination of the Gram sign of a microorganism by the original procedure or any of the many subsequently described modifications is not a routine operation. In order to ensure accurate results, training, skill, proper technique and attention to detail are required. As a consequence, alternative procedures for Gram sign determination have been sought.

U.S. Pat. No. 4,225,669 to Melnick discloses a composition for staining both Gram-negative and Gram-positive microogranisms comprising a chelating agent and a non-fluorescent dye operative at a basic or neutral pH. Determination of the Gram sign may be carried out subsequent to staining by an acid wash which decolorizes the Gram-positive microorganisms.

Attempts to adapt staining with fluorescent dyes to Gram sign determinations have been disclosed. Staining of microogranisms with fluorescent dyes is well known and Gram-negative and Gram-positive microorganisms show different staining characteristics with fluorescent dyes. Govoronov et al., Microbiology 51, 587 (1982) reported that ethidium bromide (EB) does not stain intact E. coli cells because the dye does not penetrate the cell membranes, but that staining does occur if carried out in the presence of ethylenediamine tetraacetic acid, EDTA. Matsuyama, Microbiology Letters 21, 153 (1984), observed that rhodamine 123 stained twelve Gram-positive bacteria, but seven of fourteen Gram-negative strains were sparsely stained. One of the Gram-negative strains, Salmonella minnesota, stained only after treatment with EDTA.

U.S. Pat. No. 4,094,745 to Scholefield teaches a method for staining microrganisms in food samples with a fluorochrome in the presence of phosphate ions. A protocol to detect non-viable Gram-positive and Gram-negative microorganisms in a milk sample and to determine the Gram sign includes heating the microorganisms in the presence of hydrochloric acid.

U.S. Pat. No. 4,126,516 to Messing et al. discloses a growth-based method for determination of the Gram sign of an unknown microorganism. The organism is cultured in/on a growth medium containing a lipophilic fluorescent material. During growth, Gram-negative microorganisms, having a higher cell membrane lipid content, incorporate more of the lipophilic dye than Gram-positive microorganisms which have a lower cell membrane lipid content. The Gram sign of the unknown is assigned by analysis of its fluorescence emission as compared with the fluorescence emission from known Gram-negative and Gram-positive controls cultured under identical conditions.

SUMMARY OF THE INVENTION

The present invention comprises a method for the determination of the Gram sign of microorganisms by staining the microorganisms with a plurality of fluorescent dyes in the presence of a staining buffer, applying excitation energy to the stained microorganisms, observing the color of the fluorescence emission of the stained microorganisms, and assigning the positive Gram sign to microorganisms which are substantially green and the negative Gram sign to microorganisms which are substantially orange.

The dyes may be added sequentially or simultaneously, and the sample may be incubated briefly after the dyes are added, or between dye additions. The color of the fluorescence emission may be observed by fluorescence microscopy, flow cytometry or other like techniques.

Preferred fluorescent dye combinations are acridine orange (AO)-propidium iodide (PI) and chrysaniline (CA)-PI. In a particularly preferred embodiment of the invention, the microorganisms are stained in a fluid sample. The fluid sample may be, for example, a body fluid sample containing microorganisms, such as urine, or it may be a liquid growth medium into which the microorganisms are inoculated and, if desired, allowed to grow before staining, or it may be a vehicle, such as buffer, water or saline, in which the microorganisms are suspended after transfer from another source, as, for example, from a solid growth medium.

The method of the present invention provides significant advantages over conventional methods for determination of the Gram sign. In the original Gram stain and all modifications thereof, overstaining or overdecolorizing are problems which may give the wrong result. Great care must be exercised to stay within the recommended limits for all reagent quantities and time durations for the various steps, and as a consequence, Gram-positive and Gram-negative controls are recommended. The method of the present invention avoids such restrictions, is a substantially faster and less complicated protocol, and does not require a decolorizer or mordant. No time consuming growth step is necessary. No harsh reagents or conditions, such as acid, alkali or heat which may effect the viability of the microorganisms are required. The staining may be done in a wet preparation rather than the conventional dry smear, and is therefore far less messy. Objective results may be obtained by flow cytometry which are more accurate than subjective results obtained conventionally with a microscope.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention, and is not to be limited to the embodiments illustrated. The scope of the invention will be measured by the appended claims and their equivalents.

The present invention is a method for determination of the Gram sign of microorganisms by staining with a pluarlity of fluorescent dyes wherein Gram-positive microorganisms stain one color and Gram-negative microorganisms stain a different color. The Gram sign of any microorganism can be determined by the method of the invention, as, for example, Gram-positive microorganisms such as *Staph. saprophyticus, Lactobacillus casei, Lactobacillus monocytogenes, Strep. faecalis, Candida albicans,* and the like, and Gram-negative microorganisms such a *E. coli, Proteus mirabilis, Pseudo. aeruginosa, H. influenzae, N. meningitidis, Klebs. pneumonia* and the like.

The microorganisms to be fluorescently stained for Gram sign determination may be from any source. For example, they may be present in a body fluid. Thus, it may be desired to determine the Gram sign of microorganisms in a urine sample from a patient having, or suspected to have bacteriuria, or in a blood sample from a bacteremic patient. In the latter case, the microorganisms may be stained after suitable treatment of the blood, such as, for example, by removal of the formed elements. For purposes of illustration of the present invention, it is convenient to grow microorganisms in a suitable medium to mid-log phase and use these microorganisms for fluorescent staining. It is understood, however, that microorganism growth is not a feature of the invention.

The microorganisms may be stained directly on a microscope slide, or, preferably on a suspension of the microorganisms in a suitable fluid. The fluid may be a liquid growth medium, such as colombia broth, thiogylcolate broth, Mueller-Hinton broth, or, preferably, trypticase soy broth, as for example, Trypticase Soy Broth TM, BBL Microbiology Systems, Cockeysville, Md. (hereinafter referred to as TSB TM) into which the microorganisms have been inoculated, and, if desired, grown. Alternatively, the microorganisms may be isolated from the liquid growth medium or from a body fluid such as urine or blood by any suitable technique, such as filtration or centrifugation, and resuspended in a different fluid, such as water, normal saline or a buffer such as, for example, phosphate buffer saline, or borate buffer. In another embodiment of the invention, the microorganisms may be transferred from a solid growth medium, such as trypticase soy agar, colombia agar or MacConkey agar, and suspended in the fluid for staining. The concentration of the microorganisms in the fluid suspension may be from about $1 \times 10^4$ to $1 \times 10^{10}$ colony forming units (cfu) per milliliter, preferably from about $1 \times 10^5$ to $1 \times 10^8$ cfu/ml.

A staining buffer is added to the fluid suspension of microorganisms before dye addition. Any suitable buffer may be used. Exemplary of buffers which may be used is an aqueous composition containing sodium borate, ethylenediamine tetraacetic acid (EDTA), formaldehyde and a surface active agent. Any suitable surface active agent, such as, for example, octyl phenoxy polyethoxyethanol or polysorbate 20 may be used. These reagents may be present in the buffer in concentrations of 40–200 mM, 24–100 mM, 0.02 to 0.1% and 0.02 to 0.1% by volume.

After addition of the staining buffer, the microorganisms in the fluid are stained with a combination of fluorescent dyes. Any suitable dye combination may be used, such as PI-acriflavin and PI-quinacrine. Preferred dye combinations are PI-AO and PI-CA. The dyes are preferably added to the fluid suspension as stock solutions of from about 0.0001 to about 0.01%, preferably about 0.001% in a suitable solvent, preferably water. (All percentages used herein are by weight unless otherwise indicated). The amount of stock solution of the dyes to be added will be calculated to provide a final dye concentration of from about 0.1 to about 100 ug/ml, preferably from about 1 to 50 ug/ml.

The dyes may be added simultaneously or sequentially. In either case, an optional incubation step, as described below, may be carried out after addition of the dyes. In addition, if the dyes are added sequentially, the mixture of microorganisms in fluid suspension may be incubated between dye additions. Incubation may be carried out for about 1 to 60, preferably for about 1 to 20 minutes. The temperature of incubation may be from ambient to about 50° C. Preferably, incubation is carried out at ambient temperature. It is understood that the aforementioned incubation periods serve to enhance dye absorption and are not concerned with promoting organism growth.

The staining buffer and dyes may be combined in a staining composition and the composition added to the suspension of microorganisms. The staining composition may be prepared by adding the fluorescent dyes to the staining buffer. The dyes are conveniently added to the buffer as the aforementioned stock solutions and are added in sufficient quantity to provide final dye concentrations in the staining composition of from about 1 to 100 ug/ml. The pH of the staining composition may be adjusted with an alkali metal hydroxide to 7–10, preferably 8.5 to 9.5. Sufficient staining composition is added to the suspension of microorganisms to provide a final concentration of dye in the fluid suspension of microorganisms of from about 0.1 to 100, preferably 1 to 50 ug/ml, as described above.

The stained sample may be analyzed by detection of fluorescence emission. A suitable aliquot of the sample may be withdrawn and spread over a microscope slide and observed visually by fluorescence microscopy for about 1 minute to 1 hour. The wavelength of the incident light used for excitation depends on the dyes used, and may be from about 400 to 500, preferably from about 450 to about 490 nm.

Fluorescence emission may be detected at a wavelength above 500 nm, preferably from about 500 to 700 nm. Microorganisms emitting substantially green fluorescence (500 to 550 nm) may be assigned as Gram-positive, and microorganisms emitting substantially orange fluorescence (550 to 650 nm) may be assigned as Gram-negative. Analysis may also be carried out by spectrofluorometry or, preferably, by flow microfluorometry techniques. These procedures are particularly advantageous when the microorganisms are present at low levels. In flow microfluorometry techniques, cells which are either naturally fluorescent or labeled with a fluorochrome, are passed, one at a time, through the focused beam from a light source, such as a laser or an arc lamp, whereby they are caused to emit fluorescent signals which are detected. A flow microfluorometry instrument such as a FACS Analyzer or a FACS IV Cell Sorter (FACS Division of Becton, Dickinson and Company, Sunnyvale, Calif.) may be used. The sample is preferably passed through the beam at a rate of from about 0.05 ml/min to about 0.3 ml/min., preferably about 0.1 ml/min.

In accordance with the method of the invention wherein fluorescence emission is observed using a flow microfluorometer, data may be obtained using multiple parameters of analysis, as, for example, forward and 90° light scatter and red and green fluorescence emission. The data may be presented and studied using a linear scale or, preferably, a logarithmic scale, or, if desired, some parameters may be studied using a linear scale while others are studied using a log scale. The determination of suitable parameters of analysis and instrument settings are well known to those skilled in the art and no further details in these respects are needed for a complete understanding of the invention. The data collected may be analyzed, for example, by dividing log green fluorescence emission by log red fluorescence emission to give a ratio. Gram-negative microorganisms show a ratio of 40 or less and Gram-positive microorganisms show a ratio of 45 or more. The Gram sign of an unknown microogranism may thus be assigned by the magnitude of the ratio.

The following examples are provided to further illustrate the invention, but are not to be construed in any way as limitative of the invention.

EXAMPLE 1

Staph. saprophyticus, Strep. faecalis, L. casei, L. monocytogenes, E. coli, P. mirabilis, Pseudo. aeruginosa, H. influenzae, N. meningitidis and Klebs. pneumoniae were grown separately in TSB TM to mid log phase. The organisms were separated from the growth medium and separate suspensions of ca. $10^6$ microorganisms of each species were prepared in buffer (sodium borate (4.0 g), EDTA (2 g), 10% aqueous formaldehyde (0.9 ml), polysorbate 20 (0.5 ml), and octyl phenoxy polyethoxyethanol (0.15 ml), diluted to 100 ml with water and adjusted to pH 9.2 with sodium hydroxide). Aliquots of 500 ul from each suspension were added to separate tubes, and each tube was treated with 2000 ul of the above buffer and 100 ul of 0.001% AO stock solution. The contents of the tubes were mixed and allowed to stand for 15 min. at room temperature. All tubes were treated with 100 ul of 0.001% PI stock solution and the contents of th tubes were mixed. The tubes were allowed to strand at room temperature for 15 minutes and the microorganisms were analyzed on the FACS IV Cell Sorter. The excitation wavelength was 488 nm, and data were gathered using log forward scatter, log 90° scatter, log red fluorescence emission, and log green fluorescence emission. Ratios were calculated by dividing log green fluorescence by log red fluorescence. The results are given in the Chart.

CHART

| | | | | | |
|---|---|---|---|---|---|
| | N | | | | |
| | N | | | | |
| | NN | | P | | |
| | NN | | PP | P | |
| 30 | 35 | 40 | 45 | 50 | 55 |

Fluorescence Ratio
(Log Green/Log Red)

| Gram Negative (N) | Gram Positive (P) |
|---|---|
| H. influenzae | Staph. saprophyticus |
| N. meningitidis | Strep. faecalis |
| Klebs. Pneumoniae | L. casei |
| Pseudo. aeruginosa | L. monocytogenes |
| E. coli | |
| Pr. mirabilis | |

It is seen that the ratios obtained for all Gram negative microorganisms are less than 40 and the ratios obtained for all Gram positive microorganisms are 45 or more.

EXAMPLE 2

The procedure of Example 1 was repeated except the microorganisms were suspended in water or sterile filtered urine before addition of the staining buffer. The results were similar to those given in Example 1, and the Gram signs of the microorganisms were assigned as positive or negative depending upon whether the ratios were 45 or more or 40 or less respectively.

Thus, the invention provides a method to determine the Gram sign of microorganisms based on staining with a plurality of fluorescent dyes in the presence of the staining buffer. In a preferred embodiment of the invention, the microorganisms are stained in a fluid suspension, the fluorescent dyes are AO and PI, and Gram-positive and Gram-negative microorganisms are stained substantially green and orange, respectively. In a particularly preferred embodiment of the invention, the fluorescence emission of the stained microorganisms is studied by flow microfluorometry and the Gram assignment is based on the magnitude of the log green/log red fluorescence emission ratio. The method is clean and uncomplicated, and provides the Gram assignment much faster than by conventional Gram sign protocols or by prior art methods based on fluorescent staining.

What is claimed is:

1. A method for the rapid determination of the Gram sign of microorganisms in a fluid sample comprising adding a staining buffer and a fluorescent dye to a fluid sample to provide a first mixture, incubating said first mixture, additing propidium iodide to said mixture to provide a second mixture, incubating said second mixture wherein absorption of said fluorescent dye in conjunction with absorption of said propidium iodide provides fluorescently stained microorganisms, applyihg excitation energy to said second mixture, observing the color of the fluorescence emission of the stained microorganisms, and assigning the positive Gram sign to microorganisms which fluoresce substantially green and the negative Gram sign to microorganisms which fluoresce substantially orange.

2. The method in accordance with claim 1 wherein said fluorescent dye is selected from the group of dyes consisting of acridine orange, acriflavin, quinacrine and chrysaniline.

3. The method in accordance with claim 1 wherein Gram-negative microorganisms included in said fluid sample are selected from the group of microorganisms consisting of *Escherichia coli, Proteus mirabilis, Pseudomonas aeruginosa, Klebsiella pneumoniae, Haemophilus influenzae,* and *Neisseria meningitidis.*

4. The method in accordance with claim 1 wherein Gram-positive microorganisms included in said fluid sample are selected from the group of microorganisms consisting of *Staphylococcus saprophyticus, Streptococcus faecalis, Lactobacillus casei, Lactobacillus monocytogenes* and *Candida albicans.*

5. The method in accordance with claim 1 wherein said fluid is selected from the group of fluids consisting of water, a suspending buffer, normal saline, a liquid growth medium and a body fluid.

6. The method in accordance with claim 1 wherein said excitation energy is from about 400 to about 500 nm and said fluorescence emission generated by said fluorescently stained microorganisms is observed above 500 nm.

7. The method in accordance with claim 1 wherein the fluorescence emission of said stained microorganisms is observed by flow microfluorometry.

8. The method in accordance with claim 1 wherein the fluorescence emission of said stained microorganisms is observed by fluorescence microscopy.

9. The method in accordance with claim 1 wherein said staining buffer comprises sodium borate, formaldehyde, ethylenediamine tetraacetic acid and a surface active agent.

10. A method for the rapid determination of the Gram sign of microorganisms in a fluid sample comprising adding a staining buffer and acridine orange to a fluid sample to provide a first mixture, incubating said first mixture, adding propidium iodide to said first mixture to provide a second mixture, incubating said second mixture so that it includes fluorescently stained microorganisms, applying excitation energy to said second mixture, observing the color of the fluorescence emission of the stained microorganisms, and assigning the positive Gram sign to said microorganisms which fluoresce substantially green and the negative Gram sign to said microorganisms which fluoresce substantially orange.

* * * * *